(12) United States Patent
Kato et al.

(10) Patent No.: US 6,375,809 B1
(45) Date of Patent: Apr. 23, 2002

(54) PROCESS FOR STERILIZING ARTICLES AND PROCESS FOR WRAPPING ARTICLES

(75) Inventors: Ryo Kato; Kiyoshi Suzuki, both of Kanagawa; Toyohiko Doi, Tokyo, all of (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 09/581,245
(22) PCT Filed: Nov. 10, 1998
(86) PCT No.: PCT/JP98/05071
§ 371 Date: Jun. 26, 2000
§ 102(e) Date: Jun. 26, 2000
(87) PCT Pub. No.: WO99/33496
PCT Pub. Date: Jul. 8, 1999

(30) Foreign Application Priority Data

Dec. 26, 1997 (JP) .............................. 9-369390

(51) Int. Cl.$^7$ .............................. C02F 1/461; C25F 1/00
(52) U.S. Cl. .............................. 204/157.15; 204/158.2; 205/701; 205/742
(58) Field of Search .................. 204/157.15, 158.2; 205/701, 742

(56) References Cited

U.S. PATENT DOCUMENTS 3,616,355 A * 10/1971 Themy et al. .............. 204/149
5,549,798 A * 8/1996 Kitajima et al. ............ 204/222

FOREIGN PATENT DOCUMENTS

| JP | 04-094785 A | * | 3/1992 |
| JP | 08-071136 A | * | 3/1996 |
| JP | 2627100 | | 4/1997 |
| JP | 09-154924 A | * | 6/1997 |
| JP | 9-253651 A | * | 9/1997 |

* cited by examiner

Primary Examiner—Edna Wong
(74) Attorney, Agent, or Firm—Oblon, Spivak, McClelland, Maier & Neustadt, P.C.

(57) ABSTRACT

The invention provides a method of sterilizing products and a method of packaging them, which little denature of the products, little concern with rusting or corrosion of the equipment, permit a safe working environment, and can shorten the treatment time, and this invention relates to a method of sterilizing products by adding hydrochloric acid to water not containing sodium chloride, passing the resulting fluid to a diaphragm-less electrolytic bath, electrolyzing the fluid, collecting the electrolytic water, diluting the collected electrolytic water with water, and sterilizing products with both the diluted electrolytic water and ultraviolet radiation; and to a method of packaging products with packaging members sterilized by the above process.

5 Claims, 1 Drawing Sheet

US 6,375,809 B1

PROCESS FOR STERILIZING ARTICLES AND PROCESS FOR WRAPPING ARTICLES

BACKGROUND OF THE INVENTION

1. Field of the Invention

The present invention relates to a method of sterilizing products and a method of packaging products.

In more detail, the present invention relates to a method of sterilizing products using in combination ultraviolet rays and electrolytic water obtained from water not containing sodium chloride, and to a method of hygienically packaging products using in combination the aforesaid electrolytic water and ultraviolet rays.

In the present invention, the term "product" means food and drugs.

Also, in the present invention, "practically neutral" means having a pH close to neutral, and means in particular being in a pH range of 5.0 to 6.5.

2. Description of the Related Art

Previously, as methods of sterilizing products, various methods such as heating sterilization, chemical sterilization, or irradiation sterilization have been practiced; known methods of irradiation sterilization include irradiation with γ rays, x rays, or ultraviolet rays. Also, methods using chemicals include for example methods using halogen-based sterilizing agents such as chlorine or iodine, methods using oxygen-based sterilizing agents such as hydrogen peroxide or ozone, and methods using gaseous sterilizing agents such as ethylene oxide or propylene oxide. Of these methods, hydrogen peroxide is employed in a wide range of applications on account of the vigorous oxidizing action of the oxygen which it generates (see "New Food Product Sterilization Engineering" by Isao Shibazaki, August 1983, Korin Company Limited).

As described above, in particular in the field of food products, various methods of sterilization are employed. In particular in packaging products using a packaging member, sterilization of the packaging member is performed in order to guarantee hygiene. That is, in for example retort food products, except for the case where sterilization is conducted after packaging the food product, when packaging the food product, it is important to package this in a hygienic condition by thoroughly sterilizing the packaging member.

For sterilizing a packaging member, the various sterilization methods described above may be used alone or in combination. For example, taking the case of a filling machine for filling paper containers with cream soup, the packaging member is a paper container, this paper container is sterilized by bringing it into contact with 0.1% hydrogen peroxide then irradiating it with ultraviolet rays, after which it is filled with separately sterilized cream soup, sealed and packaged (see for example WO 80/01457, Catalogue of Tetrapack Inc.).

However, in recent years, the sterilizing effect of electrolytic water obtained by electrolysis of various solutions has become known, and methods of sterilization using such electrolytic water have been established. For example, sterilization by a combination of ultraviolet rays and electrolytic acidic water, by replacing the 0.1% hydrogen peroxide referred to above by electrolyzed water, may be considered (Laid-Open Japanese Patent Publication No. 9-154924. Hereinbelow this will be referred to as the prior art).

In this prior art, "electrolytic water" is taken to mean ordinary conventional electrolytic water; such conventional ordinary electrolytic water was obtained by electrolysis of water to which sodium chloride had been added (Japanese Patent No. 2627100).

In this prior art referred to above, since electrolytic water obtained by electrolysis of water to which sodium chloride had been added was employed, there was a residual content of sodium chloride tending to cause contamination of the equipment by sodium chloride.

This therefore gave rise to the problem that crystals of sodium chloride might be deposited on the surface of the sterilized product or, if used for product packages, sodium chloride might be left behind on the packaging member affecting the taste of the packaged food product.

A further problem was that sodium chloride gave rise to various difficulties as far as the equipment was concerned, such as corrosion being caused by adhesion of sodium chloride to metal surfaces of the equipment, making this method unsuitable for use over a long period.

Furthermore, in the prior art referred to above, the electrolytic water was usually used in a strongly acidic condition. However, the dissolved condition of chlorine in strongly acidic electrolytic water is unstable so the dissolved chlorine is volatilized in a short time as chlorine gas, giving rise to the problem of instability of the sterilization effect. In order to ensure a satisfactory sterilization effect, it was therefore necessary to set the chlorine concentration of the electrolytic water beforehand at a high level. This was therefore undesirable in view of the problem of corrosion of metallic surfaces by the chlorine or in regard to safety of the working personnel etc.

Furthermore, in the prior art referred to above, when ultraviolet irradiation was performed, it was necessary to perform irradiation with ultraviolet rays for a long time of 10 seconds or more, preferably more than 30 seconds. This led to the problem, in for example, a machine for packing cream soup, that the treatment time when performing sterilization of the paper container was long, lowering the overall productive capacity. That is, this prior art was unsuited to mass production and its industrial utilization as a method for packaging products was attended by many difficulties.

Specifically, the prior art referred to the above using conventional electrolytic water suffered from the problems of being unsatisfactory in regard to product quality, equipment life, maintenance and management, ensuring the safety of working personnel, and of being unsuited to mass production.

SUMMARY OF THE INVENTION

The present invention provides a method of sterilizing products and a method of packaging products, that little denature the products, little concern with rust or corrosion and the like of the equipment, that affords a safe working environment, and can shorten the treatment time.

The present invention relates to a method of sterilizing products, which comprises adding hydrochloric acid to water not containing sodium chloride, passing the resulting fluid through a diaphragm-less electrolytic bath, subjecting the resulting fluid to electrolysis, collecting the electrolytic water, diluting the electrolytic water with water, and then sterilizing the products with both the diluted electrolytic water and ultraviolet rays, and to a method of packaging products with packaging members sterilized by the above process.

With the method of sterilizing products according to the present invention, outstanding benefits are obtained such as that 1) since no residue of sodium chloride is left after sterilization, there is no concern regarding rusting of metallic surfaces of the equipment due to sodium chloride, 2) since the electrolytic water is practically neutral and of low chlorine concentration, there is little corrosion of metallic surfaces due to oxygen and chlorine and the safety of the working environment is high, and 3) there is little risk of denaturing the products, and the treatment time is short.

Also, the method of packaging products according to the present invention has outstanding benefits such as that 1) since there is no residue of sodium chloride after packaging, there is no denaturing of products due to sodium chloride, and, in addition, there is no concern regarding rusting due to sodium chloride of the metallic surfaces of the packaging equipment, 2) since the electrolytic water that is used is practically neutral and of low chlorine concentration, there is little likelihood of corrosion due to oxygen and chlorine of metallic surfaces of the packaging equipment, and safety of the working environment is high, and also 3) it is suited to mass treatment.

An object of the present invention is to provide a method of sterilizing products using in combination electrolytic water and ultraviolet rays, which little denatures the products, little concerns with rust and corrosion of the equipment, permits a safe working environment, and can shorten the treatment time.

A further object of the present invention is to provide a method of hygienic packaging products combining the use of electrolytic water and ultraviolet rays, which little denatures the products after packaging, little concerns with rust and corrosion and the like of the packaging equipment, permits a safe working environment, and which is suited to mass treatment.

In order to solve the above problem, according to a first aspect of the present invention there is provided a method of sterilizing products, which comprises adding hydrochloric acid to water not containing sodium chloride, passing the resulting fluid through a diaphragm-less electrolytic bath, subjecting the resulting fluid to electrolysis, collecting the electrolytic water, diluting the electrolytic water with water, and then sterilizing the products with both the diluted electrolytic water and ultraviolet rays.

Also, in preferred embodiments of the first aspect of the present invention, the products are sterilized by bringing diluted electrolytic water into contact with the surface of the products, and then irradiating the products with ultraviolet rays (hereinbelow called the first embodiment), the diluted electrolytic water is of active chlorine concentration 3 to 50 ppm, in particular under 20 ppm (hereinbelow called the second embodiment) and the diluted electrolytic water is neutral (hereinbelow called the third embodiment).

In order to solve the above problem, according to a second aspect of the present invention, there is provided a method of packaging products by means of a hygienic packaging member, which comprises adding hydrochloric acid to water not containing sodium chloride, passing the resulting fluid through a diaphragm-less electrolysis bath, subjecting the resulting fluid to electrolysis, collecting the electrolytic water, diluting the electrolytic water with water, bringing the diluted electrolytic water into contact with the packaging member, irradiating this packaging member with ultraviolet rays, and then packing the products by the sterilized packaging member.

Also, according to preferred embodiments of the second aspect of the present invention, the diluted electrolytic water is of active chlorine concentration 3 to 50 ppm, in particular under 20 ppm (hereinbelow called the fourth embodiment), the diluted electrolytic water is practically neutral (hereinbelow called the fifth embodiment) and the packing member is irradiated with ultraviolet rays for under 10 seconds (hereinbelow called the sixth embodiment).

Next, the present invention will be described in more detail.

A first aspect of the present invention consists in a method of sterilizing products. According to a first aspect of the invention, first of all, hydrochloric acid is added to water that does not contain sodium chloride. In this context, the term "water" means tap water, underground water, underflow water, desalted water, distilled water, or mixtures of these and the like which contain essentially no sodium chloride. "Which contain no sodium chloride" means that no sodium chloride has been deliberately added; traces of chlorine ions and sodium ions naturally contained in the water are not taken into account.

This aqueous solution of hydrochloric acid is passed through a diaphragm-less electrolytic bath where electrolysis is conducted and from which electrolytic water is collected. This electrolytic water of course contains no sodium chloride. The above operation may be conducted by arranging a tank in which is stored hydrochloric acid of 21% concentration (by weight; Also hereinbelow unless otherwise specially indicated) in a PURE STAR (Trademark; manufactured by Morinaga Engineering Co., Ltd.), for example, which is a commercially available electrolytic water manufacturing device, supplying hydrochloric acid and tap water thereto, and continuously conducting electro-decomposition, the electrolytic water obtained being then diluted to adjust the active chlorine concentration to the prescribed range.

According to the present invention, products are sterilized by a combination of the electrolytic water which is thus obtained and ultraviolet ray irradiation. Preferably the irradiation with ultraviolet rays is conducted for no more than 10 seconds. In the prior art referred to above irradiation for more than 10 seconds was necessary, but, with the present invention, as will be clear from the embodiment given below, even when the concentration of active chlorine in the electrolytic water is low, a satisfactory sterilizing effect is obtained with ultraviolet ray irradiation of no more than 10 seconds, in particular, of a time of 2 seconds or less.

With the method of the present invention, since the electrolytic water contains no sodium chloride, there is no possibility of sodium chloride being left behind after sterilization of the products. There is therefore little risk of altering the quality of the products. Also, regarding equipment, this can withstand use for a long period without occurrence of the various troubles caused by sodium chloride, such as rusting of metallic surfaces.

In a first preferred embodiment of the present invention, the product is sterilized by bringing the surface of the product into contact with electrolytic water, then irradiating with ultraviolet rays. "Bringing into contact" in this case means an operation in which electrolytic water is made to adhere to the surface of the product; examples are an operation in which electrolytic water is sprayed or applied to the surface of the product, or an operation in which the product is immersed in electrolytic water, etc.

Also, a step may be added in which electrolytic water adhering to the product is dried before or after irradiating with ultraviolet rays.

In a second preferred embodiment of the present invention, electrolytic water of active chlorine content 3 to 50 ppm is employed.

In general, in the manufacture of electrolytic water, the pH and active chlorine concentration are determined by the following expressions (i) and (ii).

$$C_P = I \cdot 70.9 \cdot 1000 / 2F \cdot V \quad \text{(i)}$$

$$C_R = (2F \cdot C \cdot vc - I) / 2F \cdot V \quad \text{(ii)}$$

[Where, in the above expressions, $C_P$ indicates the amount of chlorine generated (ppm), I indicates the current (ampere), F indicates the Faraday constant, V indicates the amount of electrolyzed water manufactured, $C_R$ indicates the concentration of chlorine in the electrolytic water, C indicates the concentration of the undiluted hydrochloric acid (21%), and vc indicates the flow amount of undiluted hydrochloric acid, respectively.]

From the above expression (i), it can be seen that increasing the amount of supply of water decreases the concentration of active chlorine, and increasing the current increases the concentration of active chlorine, and from expression (ii) it can be seen that increase of the amount of supply of hydrochloric acid or decrease of the current results in increase of the density of hydrochloric acid, while increase of the amount of manufacture of electrolytic water decreases the concentration of hydrochloric acid. Electrolytic water of the desired concentration of active chlorine can therefore be obtained by suitably adjusting the amount of supply of hydrochloric acid, amount of supply of water, and current, or by diluting the electrolytic water after electrolysis.

In general, in water in which chlorine is dissolved, the chlorine takes three modes, namely, molecular chlorine, hypochlorous acid, and hypochlorous acid ions; the proportion in which these are present changes depending on the pH value, but, of these three modes, hypochlorous acid is said to have the strongest sterilizing effect ("Hygiene Test Methods Annotated And Explained 1990" published by the Japanese Pharmaceutical Association (Nippon Yaku Gakkai), page 946, Mar. 31, 1990).

The present invention makes use of the powerful sterilizing action of hypochlorous acid, and enables this to be employed in a range of active chlorine concentration of 3 to 50 ppm. Also, a fully satisfactory sterilizing effect is obtained even in a low range of active chlorine concentration i.e. less than 20 ppm and in particular, as will be clear from the following test examples, a range of 3 ppm to 20 ppm is particularly suitable. Specifically, since, with the method of sterilization of the present invention, the chlorine concentration of the electrolytic water is lower than in the prior art, there are the benefits that there is no chemical smell after sterilization of products, there are no adverse effects due to chlorine even if it comes into contact with the hands of the workers, and there is little concern regarding corrosion due to chlorine of metallic surfaces etc. of the equipment; thus all in all, its safety in regard to products, equipment and working environment is high.

In a third preferred aspect of the present invention, the electrolytic water is employed in practically neutral condition. "Practically neutral" means a pH range of 5.0 to 6.5; in this range, the concentration of hypochlorous acid referred to above is highest. Also, materials of poor resistance to acidity can also be employed in the equipment and the electrolytic water is safe even when it comes into contact with the skin of workers.

A second aspect of the present invention consists in a hygienic product packaging method utilizing the sterilization method constituting a first aspect of the invention.

According to the second aspect of the invention, electrolytic water is prepared, not containing sodium chloride, just as in the case of the first aspect of the invention. The packaging member is then sterilized by bringing this electrolytic water into contact with the packaging member, followed by irradiating it with ultraviolet rays. After the packaging member has been sterilized, the product is packaged by ordinary methods to obtain the package.

Since the electrolytic water employed in the present invention does not contain sodium chloride, there is no possibility of common salt being left behind on the packaging member, so there is absolutely no risk of denaturing of the product due to sodium chloride.

Also, since there is little rusting of metallic surfaces due to residual sodium chloride, the packaging equipment can be used over a long time; this is also advantageous from the point of view of maintenance and manufacturing costs.

According to a fourth aspect of the present invention, electrolytic water of active chlorine concentration 3 to 50 ppm, preferably 3 ppm to 20 ppm is employed. According to the present invention, electrolytic water of low active chlorine content can be employed. Consequently, the various troubles caused by chlorine are minimized and high safety is achieved in regard to the equipment and working environment.

According to a fifth aspect of the present invention, the electrolytic water used is employed in a practically neutral condition. Materials of poor resistance to acids can therefore be employed in the packaging equipment and it is safe even if allowed to come into contact with the skin of workers.

According to a sixth aspect of the present invention, irradiation by ultraviolet rays is conducted for up to 10 seconds, preferably for a time of under 2 seconds. As mentioned above, according to the present invention, irradiation with ultraviolet rays for a short time is fully sufficient and, as a result, in particular when processing using a continuous process, treatment speed is increased, enabling production capacity to be raised.

It should be noted that there are no restrictions regarding the type of packaging member according to the present invention and, apart from paper containers as mentioned above, it could be applied to various packaging members such as molded plastics containers, bottles, cans, paper sheet, or laminate.

Also, in the present invention, it is desirable that the diaphragm-less electrolytic bath should be a multi-electrode type electrolytic bath.

In general, there are two types of arrangement whereby a plurality of electrodes may be coupled in an electrolytic bath, namely, a single-electrode arrangement and a multi-electrode arrangement. The single-electrode arrangement is an arrangement in which all of the electrodes are connected to one or other of the negative terminal or positive terminal of the power source; the multi-electrode arrangement is an arrangement in which for example there is provided a construction in which a plurality of electrodes are superimposed with fixed separations, being mutually insulated, there being at least one intermediate electrode, that is not connected to either terminal, between the electrodes (i.e. positive electrodes) connected to the positive terminal of the power source and the electrodes (i.e. negative electrodes) connected to the negative terminal of the power source.

Also, in this case, it is desirable that, when conducting electrolysis, the voltage per electrode pair should be at least 1.5 volts and less than 4.0 volts. In the case of a multi-electrode electrolytic bath, as mentioned, an intermediate electrode is present between the negative electrode and positive electrode, but the term "voltage per electrode pair" means the voltage between two adjacent electrodes, including the negative electrode, positive electrode and intermediate electrode.

In general, when the voltage of the electrolytic bath is raised, chlorine starts to be generated at 1.3 volts or more, and the maximum rate of evolution is reached at 1.5 volts or more. It is therefore desirable that the voltage per electrode pair should be at least 1.5 volts. Also, if the voltage exceeds 4.0 volts, oxygen starts to be generated and if 5.0 volts is exceeded, ozone starts to be generated. Generation of ozone is undesirable and generation of oxygen wastes power, so preferably the voltage should be below 4.0 volts. From the economic viewpoint, in particular, it is preferable that the voltage should be below 3.0 volts.

Next, the present invention will be described in detail with reference to test examples.

TEST EXAMPLES

These tests were conducted in order to ascertain the relationship between the sterilization conditions of the packaging member in a method of packaging of products according to the present invention and the sterilization effect.

1) Preparation of Samples

Samples of cream soup in paper containers were manufactured by the same method as in the case of Example 1, to be described, using the paper container filling machine 1 illustrated in Example 1 (see FIG. 1), with the exception that, by altering the current of the diaphragm-less electrolytic bath 14 in electrolytic water generating system 10 and altering the degree of dilution of the electrolytic water, the active chlorine concentration of the electrolytic water was altered to 2.0 to 20.0 ppm as shown in Table 1 and, by altering the feed speed of conveyor belt 2, the ultraviolet ray irradiation time was altered to 0.5 to 25.0 seconds as shown in Table 1. These were taken as samples of the present invention.

Also, as a comparative example, samples of cream soup packed in paper containers were manufactured by the same method as in Example 1 below by adding common salt to a diaphragm-less electrolytic bath 14 and using the electrolytic water obtained by electrolysis (active chlorine concentration 25.0 ppm) in the same way, irradiating with ultraviolet rays for 0.5 to 25.0 seconds. These were taken as comparative example samples.

2) Test Methods (1) Flavor Test

The flavor of the samples according to the present invention and the comparative samples were compared by a flavor panel of 20 men and women.

(2) Storage Test

The samples obtained were all stored in a refrigerator at 10° C., the packages opened on the 14th day, and the flavor ascertained, and the number of ordinary bacteria and the number of psychrophillic bacteria determined by the ordinary methods ("Food Product Microorganism Handbook", pages 560 to 576, published by Gihodo Shuppan Company Limited, Nov. 1, 1995, compiled by Yoshii et al.), the satisfactoriness of the product being thereby determined.

3) Test Results (1) Flavor Test

Six of the 20 flavor panelists evaluated the sample of the comparative example as having a bad flavor apparently due to salt, chlorine or acidity.

As a supplementary opinion, of the samples according to the present invention, three panelists evaluated the samples whose active chlorine concentration was under 19.5 ppm as having better flavor than those whose active chlorine concentration was 20.0 ppm.

(2) Storage Test

The results of this test are shown in Table 1. Table 1 is a Table showing the relationship between the sterilization conditions (active chlorine concentration of the electrolytic water and ultraviolet ray irradiation time) of a packaging member in the method of packaging products according to the present invention and storage characteristics after packaging. In Table 1, ○ indicates samples that were found to be good products, being negative in respect of ordinary bacteria and psychrophillic bacteria and × indicates samples that were found to be defective products on account of one or other or both of ordinary bacteria or psychrophillic bacteria being detected.

From Table 1, it can be seen that, with the samples of the present invention, if the active chlorine concentration of the electrolytic water was at least 3 ppm, even if the ultraviolet ray irradiation time was less than 10 seconds, fully satisfactory sterilization was achieved; in particular it was found that ultraviolet ray irradiation for 1.0 seconds or more was ideal. It should be noted that in Table 1, of the samples of the present invention, the range of active chlorine concentration 3.5 to 19.0 ppm is not shown in the Table since there is no marked difference from the cases of 3 ppm and 19.5 ppm.

Regarding the sample of the comparative example, a reasonably satisfactory sterilizing effect was found since the active chlorine concentration of the electrolytic water was the high concentration of 25 ppm.

From the above results, it was found that, with the method of packaging products of the present invention, there was no denaturing of the flavor of the products due to the packaging and furthermore products were obtained whose flavor was better than that of the prior art. Also, with the method of packaging products of the present invention, it was found that the active chlorine concentration of the electrolytic water was preferably 3 ppm to 20 ppm and an ultraviolet ray irradiation time of less than 10 seconds was fully satisfactory, 1.0 seconds or more being particularly preferable.

It should be noted that when similar tests were conducted in which the sterilization conditions of the cream soup and the capacity of the paper containers etc. were altered or other food products were employed, practically identical results were obtained.

Also, in regard to sterilization of "daikon" (giant radish) described in Example 2 below, tests were conducted likewise varying in various ways the active chlorine concentration of the electrolytic water and the ultraviolet ray irradiation time, but practically identical results were obtained; thus the test results confirmed that sterilization was equivalent in regard to ordinary products also.

TABLE 1

| Active chlorine concentration (ppm) | | Ultraviolet ray irradiation time (seconds) | | | | | | |
|---|---|---|---|---|---|---|---|---|
| | | 0.5 | 1.0 | 1.5 | 2.0 | 10.0 | 20.0 | 25.0 |
| Test examples | 2.0 | X | X | X | X | X | X | X |
| | 2.5 | X | X | X | X | 0 | 0 | 0 |
| | 3.0 | X | 0 | 0 | 0 | 0 | 0 | 0 |
| | 19.5 | 0 | 0 | 0 | 0 | 0 | 0 | 0 |
| | 20.0 | 0 | 0 | 0 | 0 | 0 | 0 | 0 |
| | 25.0 | 0 | 0 | 0 | 0 | 0 | 0 | 0 |
| Comparative example | 25.0 | 0 | 0 | 0 | 0 | 0 | 0 | 0 |

EXPLANATION OF THE REFERENCE SYMBOLS

Figure 1:
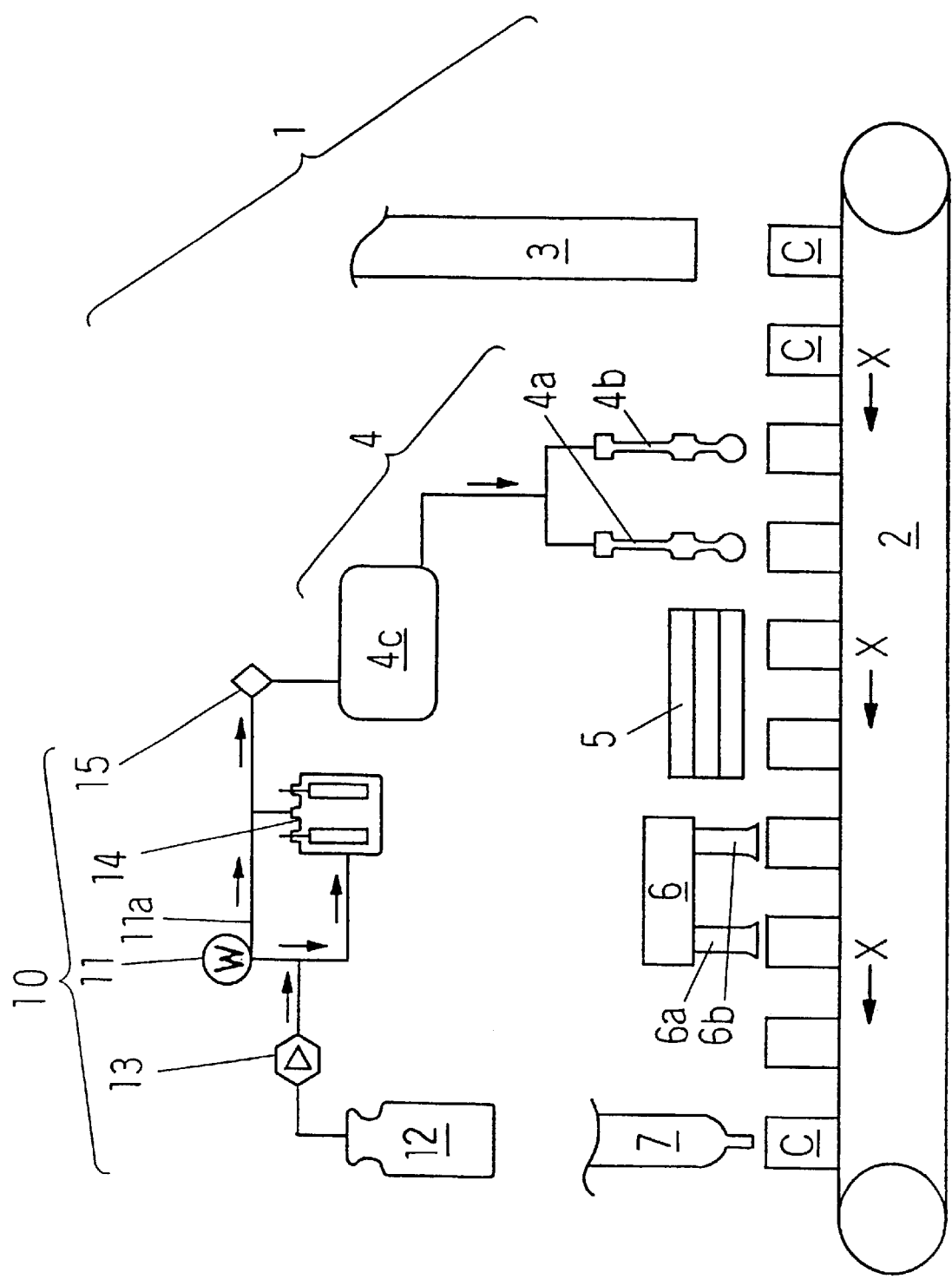
FIG. 1 is a diagram illustrating an example of a device for putting into practice the method of packaging products according to the present invention.

1 Paper container filling machine for cream soup
2 Conveyor
3 Paper container supply device
4 Spray system
5 Ultraviolet ray lamp
6 Remover
7 Filling nozzle
10 Electrolytic water generating system
11 Tap water supply source
12 Hydrochloric acid container
13 Hydrochloric acid pump
14 Diaphragm-less electrolytic bath
15 Gas separator

DESCRIPTION OF THE PREFERRED EMBODIMENTS

Next, the present invention is described in detail with reference to embodiments, but the present invention is not restricted to the following embodiments.

EXAMPLE 1

FIG. 1 is a diagram illustrating an example of a device (paper container filling machine for cream soup) for putting into practice the method of packaging products according to the present invention.

In FIG. 1, the paper container filling machine for cream soup is equipped with a conveyor 2 which feeds paper containers C in order in the direction of arrow X. On the conveyor 2, in order, from the upstream side (right-hand side in the drawing) of the conveying direction of conveyor 2 towards the downstream side (left-hand side in the drawing) there are provided: paper container supply device 3 (carton mandrel), spray system 4, ultraviolet ray lamp 5, remover 6 and filling nozzle 7. Further downstream from filling nozzle 7, there is provided a sealing device that seals paper containers C, but this is not shown in FIG. 1.

Paper container supply device 3 is a device that supplies paper containers C in formed condition. Also, the spray system 4 comprises spray nozzles 4a and 4b and tank 4c. Spray nozzle 4a and 4b are spray nozzles for spraying sterilizing agent into the interior of paper containers C and are both two-fluid nozzles. However, in FIG. 1, the piping related to the air and the flow rate adjustment valves and the like are not shown. Tank 4c stores sterilizing agent. Remover 6 is equipped with hot air nozzles 6a and 6b. Hot air is blown out of these hot air nozzles 6a and 6b to dry the interior of paper container C. Filling nozzle 7 supplies sterilized cream soup to fill the paper containers C therewith.

Paper containing filling machine for cream soup provided with the basic construction as above is equipped with an electrolytic water generating system 19 which is characterized of the present invention.

As the electrolytic water generating system 10, the "PURE STAR" (Trademark; Manufactured by Morinaga Engineering Co., Ltd.) system was employed. This "PURE STAR" system is equipped with tap water supply source 11, hydrochloric acid container 12, hydrochloric acid pump 13, diaphragm-less electrolytic bath 14 and gas separator 15.

Tap water is supplied from tap water supply source 11 and mixed by hydrochloric acid pump 13 with 21% concentrated hydrochloric acid stored in hydrochloric acid container 12, and then the resulting fluid is passed through diaphragm-less electrolytic bath 14. The electrolytic water electrolyzed in diaphragm-less electrolytic bath 14 is mixed with tap water from dilution water line 11a to dilute it, unwanted hydrogen therein is removed by gas separator 15, and then the resulting fluid is stored in tank 4c.

Next, an embodiment of a method of packaging products according to the present invention employing the paper container filling machine for cream soup of FIG. 1 will be described.

Electrolytic water manufactured beforehand by means of electrolytic water generating system 10, after adjusting active chlorine concentration thereof to 14 ppm, was stored in tank 4c. Next, paper containers C (1-liter paper packs) are supplied from paper container supply device 3 (carton mandrel) and fed in the direction of the arrow X sequentially by means of conveyor 2.

Electrolytic water stored in tank 4c is sprayed on to the inner surface of paper containers C under the condition of flow rate 300 ml/h from spray nozzles 4a and 4b, the paper containers C are passed beneath ultraviolet ray lamp 5 to irradiate them for 1.5 seconds with UV-C ultraviolet rays at 50 mW.s/cm$^2$.

Next, in remover 6, the interior of paper containers C is dried by blowing out hot air of 300° C. from hot air nozzles 6a and 6b, and then they are filled with cream soup sterilized with a scraping-type sterilizer under the conditions: 130° C., 2 seconds, from filling nozzle 7. They are then sealed by a sealing device (not shown) on the downstream side. Cream soup product packed in the paper container of 1 liter capacity was thereby manufactured with a production capacity of 6000 pieces per hour.

EXAMPLE 2

Electrolytic water, whose active chlorine concentration was adjusted to 13 ppm, was manufactured with a system 10 for generating electrolytic water not containing sodium in FIG. 1 referred to above, and stored in a vat.

Commercially available whole daikon (radish; length about 40 cm) was introduced into the vat and immersed in the electrolytic water for 10 minutes, and then the radish was pulled up out of the electrolytic water, placed in the front of three ultraviolet ray lamps 5 to irradiate it with ultraviolet rays for 5 seconds, and then immediately dried by directing a current of air at normal temperature with a drier.

Before and after performing the above operation on ten radishes for subjecting each radish to sterilizing treatment, the 5 cm square of the surface of each radish was wiped with sterilized gauze of 5 cm×5 cm, and the gauze was introduced into 10 ml of sterilized physiological saline solution containing sodium thiosulfate in 0.5% concentration; this solution was diluted by the ordinary method and cultured for 48 hours at 35° C. using a standard agar medium, and then the number of live bacteria thereof was determined by the ordinary method.

The results obtained above were converted into results for a 10 cm square wiping area and the number of live bacteria before and after sterilization of each radish were compared. As a result, it was found that, whereas the number thereof before sterilization was a mean of 1,000,000 cfu/100 cm$^2$, the number thereof after sterilization was a mean of 1,000 cfu/100 cm$^2$, representing a reduction of about $\frac{1}{1,000}$. Thus it was confirmed that in every case fully satisfactory sterilization thereof was achieved.

Comparative Example 10 radishes were sterilized in the same way as in the Example 2, except sterilizing the radishes with only electrolytic water and without performing irradiation with ultraviolet rays, and then the number of live bacteria thereof before and after sterilization were compared in the same way. As a result, it was found that, whereas the mean before sterilization was 1,000,000 cfu/100 cm$^2$, the mean after sterilization was 10,000 cfu/100 cm$^2$, representing a reduction of only 1/100. Similar results were obtained even if the immersion time in the electrolytic water was lengthened or the sterilizing operation was repeated.

INDUSTRIAL APPLICABILITY

The benefits presented by the present invention are as follows.

(1) With the method of sterilizing products according to the present invention, no sodium chloride is left after sterilization, so there is no concern regarding rusting of metallic surfaces of the equipment due to sodium chloride. This is therefore advantageous in that the equipment can withstand prolonged use and in terms of maintenance and manufacturing costs.

(2) With the method of sterilizing products according to the present invention, the electrolytic water is practically neutral, and the chlorine concentration is low, so there is little corrosion of metal surfaces due to oxygen or chlorine and the safety of the working environment is high.

(3) With the method of sterilizing products according to the present invention, the risk of denaturing the products is small and treatment time is short.

(4) With the method of packaging products according to the present invention, there is no residue of sodium chloride after packaging and no denaturing of the products due to sodium chloride and furthermore there is no concern regarding rusting of the metallic surfaces of the packaging equipment due to sodium chloride. Consequently, the packaging equipment can withstand prolonged use and advantages are obtained in respect of maintenance and manufacturing costs.

(5) With the method of packaging products according to the present invention, the electrolytic water that is employed is practically neutral and its chlorine concentration is low, so there is little likelihood of corrosion of the metallic surfaces of the packaging equipment due to oxygen or chlorine and the safety of the working environment is high.

(6) The method of packaging products according to the present invention is suited to mass treatment.

What is claimed is:

1. A method of packaging food or drugs by mass production by means of a hygienic packaging member, which comprises adding hydrochloric acid to water not containing sodium chloride, passing the resulting fluid through a diaphragm-less electrolysis bath to subject the resulting fluid to electrolysis on condition that voltage per electrode pair is below 4.0 volts, collecting the electrolytic water not generating ozone, diluting the electrolytic water with water, sterilizing a packaging member with the diluted electrolytic water, and irradiating this packaging member with ultraviolet rays, and then packing the products by a sterilized packaging member.

2. The method of packaging food or drugs according to claim 1, wherein the diluted electrolytic water not generating ozone has an active chlorine concentration of 3 to 50 ppm.

3. The method of packaging food or drugs according to claim 2, wherein the diluted electrolytic water not generating ozone has said active chlorine concentration of less than 20 ppm.

4. The method of packaging food or drugs according to claim 1, wherein the diluted electrolytic water not generating ozone is practically neutral.

5. The method of packaging food or drugs according to claim 1, wherein the packaging member is irradiated with said ultraviolet rays for under 10 seconds.

* * * * *